United States Patent [19]

Williams

[11] Patent Number: Plant 7,606

[45] Date of Patent: Jul. 30, 1991

[54] MINIATURE ROSE PLANT/MINAVCO

[76] Inventor: Ernest D. Williams, 1510 Lebanon Ave., Dallas, Tex. 75208

[21] Appl. No.: 516,713

[22] Filed: Apr. 26, 1990

[51] Int. Cl.[5] ..... A01H 5/00

[52] U.S. Cl. ..... Plt./7

[58] Field of Search ..... Plt./7-9

*Primary Examiner*—James R. Feyrer

[57] ABSTRACT

The subject of the present disclosure is a new and distinct variety of miniature rose plant characterized by warm russet color of the double flowers and by the profusion of bloom.

1 Drawing Sheet

The present invention relates to a new and distinct variety of hardy, dwarf, bush type rose plant of the miniature class; the variety being primarily characterized—as to novelty—by the warm russet coloration of the flowers which in general color effect are similar to Honey 'N Spice (Miniature variety—not patented).

The variety is further characterized by:

The abundance of bloom, with flowers usually borne singly.

Fragrant.

A plant which is vigorous, of bushy, upright shape with semi-glossy to matt, small foliage, with pointed leaflets; the buds and flowers being similar in form and size to Amberglo (miniature—not patented), but averaging fewer petals.

The plant, which has a normal height of 12-14 inches or more can easily be maintained at lesser height by occasional trimming.

A plant which grows and blooms satisfactorily outdoors; is good for growing in pots; and provides excellent garden decoration as well as cut flowers.

The present variety of miniature rose was originated by me at my nursery located at Dallas, Tex., under conditions of careful control and observation, as a cross between Tom Brown (a floribunda—not patented) as the seed parent and Twilight Trail (miniature—U.S. Plant Pat. No. 6,198) as the pollen parent.

Subsequent to origination of the variety I successfully reproduced it, at my nursery as aforesaid, by cuttings; the reproductions having run true in all respects.

The color photograph illustrates the variety, including the foliage, bud and flowers.

Referring now specifically to the new and distinct variety of miniature rose plant, the following is a detailed description thereof in outline; all major color plate identifications being by reference to the R.H.S. Colour Chart, except where common terms of color definiation are employed.

Type: Hardy; dwarf; bushy; upright; seedling; outdoors; cut flowers; garden decoration; potted plant.

Class: Miniature.

*Variety identification.*—Minavco.

*Commercial synonym.*—Sue Jo.

Flowers borne; Usually singly on slender wirey stems.

Quantity of bloom: Abundant.

Bud:

*Peduncle.*—Medium to long length; slender but sturdy; erect; medium green, sometimes tinted bronze (outdoors); hairs — few.

*Before calyx breaks; size.*—Small. Form short; pointed with several foliaceous apendages and few or no timy hairs on surface of bud; with foliaceous parts extending beyond the tip of the bud equal to one-half or less of its length. Color — medium green, occasionally tinted with bronze (outdoors).

*As calyx breaks, color.*—Russet.

*Opening.*—Opens well in all weather.

Bloom:

*Size when fully open.*—Small, averaging about 35-40 mm (1½").

*Petalage double.*—Averaging about 35 petals, arranged regularly plus sometimes several small petaloids.

*Form.*—High centered, with petals reflexing loosely outward and later at maturity, rolled loosely outward and downward. Open flowers show stamens.

Petals: Fairly thick, satiny on inside and on outside surface.

*Shape.*—Outside petals, broad lanceolate — almost round; intermediate — broad lanceolate with rounded tip; inside — lanceolate with rounded tip.

Color: Newly opened flower from a plant grown outdoors (October 1988), Dallas. Tex.

*Outside petal.*—Outside surface — near Greyed Orange Group 172-B progressing to C and D, cool weather highlight (October) on back of petal near and between Red Group 46-A and Red Group 45-A. Inside surface — yellowish near white on petal edges, lighter than Yellow Group 8-D progressing to base of petal to near and between Yellow Group 8-B and Yellow Group 9-C.

*Intermediate petal.*—Outside surface — near and between Greyed Orange Group 170-B and 168-B to near and between Greyed Orange Group 171-B and 172-B. Inside surface — similar to outside petal.

*Inner petal.*—Outside surface — same as intermediate petal; inside surface — same as intermediate petal. Mature flowers are often tinted pinkish as they age. General color effect; newly opened flowers warm russet outside and light yellow inside. Three days open — color similar to newly opened flowers but less brilliant. Behavior — opens well in all weather. Color usually becomes pinkish as flowers age. Flower longevity (October 1988) — plant in pot, 6–8 days or longer. Cut flowers at living room temperature 4–5 days or longer.

Reproductive organs:

*Stamens.*—About normal.

*Filaments.*—Varying length, yellow.

*Anthers.*—Well formed; yellow.

*Pollen.*—Above average amount.

*Pistils.*—Average number.

*Styles.*—Uneven; medium to short length; bunched; color — golden yellow.

*Ovaries.*—All enclosed in calyx.

*Hips.*—Few.

*Sepals.*—Permanent; spear shaped; recurved downward.

*Seed.*—Few.

Foliage:

*Leaves.*—Compound of five (sometimes three or seven) leaflets; fairly small; leathery; semi-glossy to matt.

*Leaflets.*—Shape: broad; nearly oval, apex acute; base rounded or rounded acute. Margin serrate. Color: medium to dark green; new growth — normal (medium) green. Rachis: medium strength; upper side may have a few tiny short prickles or hairs, grooved; underside sparsley thorny with few or no tiny prickles. Stipules: medium long; narrow points which turn out usually at about 45 degrees.

Growth:

*Habit.*—Dwarf; bushy; upright; much branched.

*Growth.*—Free vigorous; internodes short.

*Canes.*—Medium; slender; sturdy.

*Main stems.*—Color; medium green.

*Thorns.*—Few; slender nearly straight inclined slightly downward; medium length, medium oval base; color; light tan. Prickles — none. Hairs — none.

*Branches.*—Color: medium green. Thorns: few; medium length; slender; nearly straight, slightly inclined downward. Medium oval base. Prickles: none. Hairs: none.

The miniature rose plant and its flowers as herein described may vary in slight detail due to climatic, soil and cultural conditions under which the variety may be grown; the present description being of the variety as grown in Dallas, Tex.

The following is claimed:

1. A new and distinct variety of miniature rose plant of hardy, dwarf, bushy, upright, much branched habit, substantially as illustrated and described, characterized by buds and fragrant flowers of warm russet and yellow color, being of a shade generally near Greyed orange Group 172-B and Yellow Group 8-B, the bud and flower resembling the variety Amberglo (miniature not patented) in form and size but having fewer petals; and further characterized by a plant of vigorous and compact growth habit, easy to propagate from cuttings, with an abundance of flowers borne usually one to the stem.

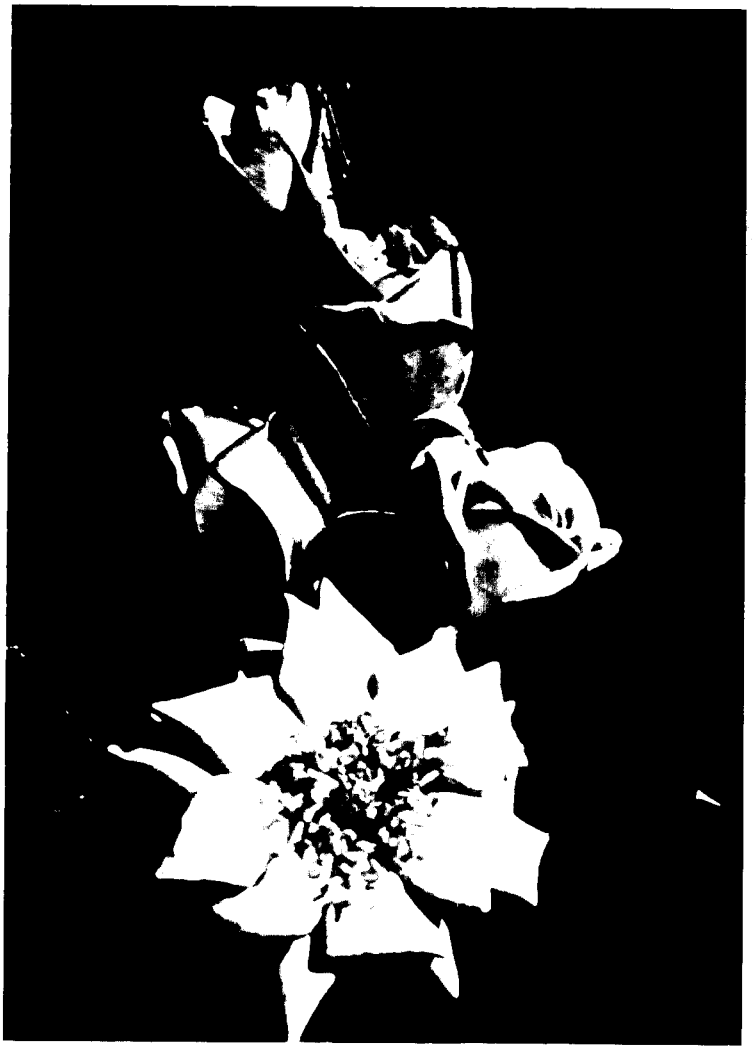

* * * * *